(12) United States Patent
Holmström et al.

(10) Patent No.: US 7,164,947 B2
(45) Date of Patent: Jan. 16, 2007

(54) HEART STIMULATOR WITH STIMULATION CONTROLLED BY ANALYSIS OF AN AVERAGE IMPEDANCE MORPHOLOGY CURVE

(75) Inventors: Nils Holmström, Järfälla (SE); Anders Björling, Järfälla (SE); Kjell Norén, Solna (SE); Karin Ljungström, Hässelby (SE); Sven Kalling, Täby (SE)

(73) Assignee: St. Jude Medical AB, Jarfalla (SE)

( * ) Notice: Subject to any disclaimer, the term of this patent is extended or adjusted under 35 U.S.C. 154(b) by 363 days.

(21) Appl. No.: 10/619,354

(22) Filed: Jul. 14, 2003

(65) Prior Publication Data

US 2004/0078058 A1    Apr. 22, 2004

(30) Foreign Application Priority Data

Jul. 22, 2002    (SE) .................................... 0202288

(51) Int. Cl.
*A61N 1/365*    (2006.01)
(52) U.S. Cl. ...................................................... 607/17
(58) Field of Classification Search .................. 607/17, 607/27, 9, 28
See application file for complete search history.

(56) References Cited

U.S. PATENT DOCUMENTS

| 4,535,774 | A |   | 8/1985  | Olson |
| 5,282,840 | A |   | 2/1994  | Hudrlik |
| 5,334,422 | A |   | 8/1994  | Myers et al. |
| 5,584,868 | A |   | 12/1996 | Salo et al. |
| 5,782,884 | A |   | 7/1998  | Stotts et al. |
| 6,223,079 | B1 |  | 4/2001  | Bakels et al. |
| 6,584,353 | B1 | * | 6/2003 | Meyer ........................ 607/27 |

FOREIGN PATENT DOCUMENTS

| EP | 0 607 511 | 7/1994 |
| EP | 0 615 770 | 9/1994 |
| EP | 0 765 671 | 4/1997 |

* cited by examiner

*Primary Examiner*—Scott M. Getzow
(74) *Attorney, Agent, or Firm*—Schiff Hardin LLP

(57) ABSTRACT

A heart stimulator for electric stimulation of a patient's heart has an impedance measuring unit that measures the impedance between at least two measurement electrodes implanted in a patient such that volume changes of at least one of the chambers of the left heart result in changes in the measured impedance. An analyzer analyzes the measured impedance for the control of the stimulation of the heart. A calculation unit calculates an average impedance morphology curve during a time interval of several cardiac cycles. The analyzer analyzes the average impedance morphology curve for use for the control of the stimulation to optimize the patient hemodynamics.

19 Claims, 3 Drawing Sheets

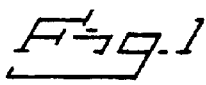
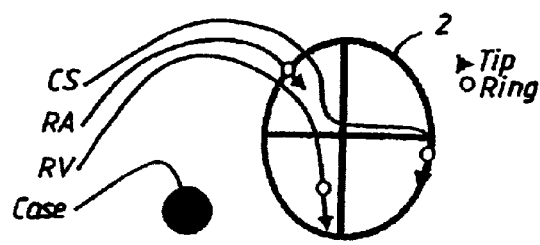
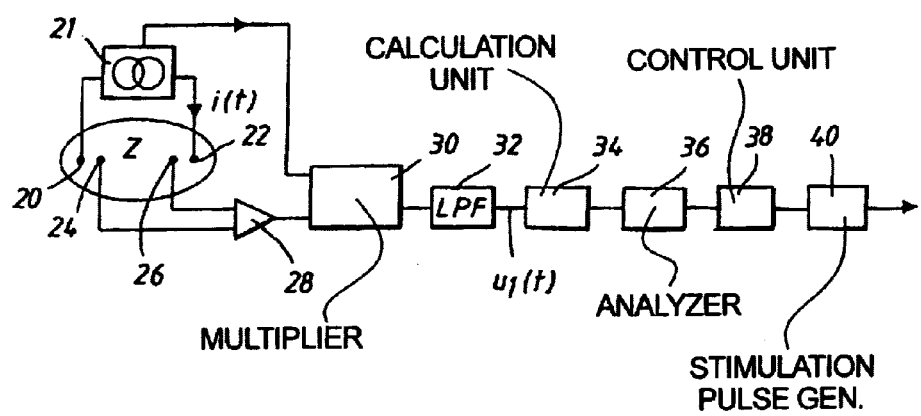

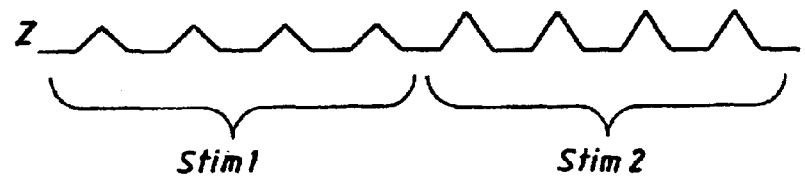
Fig. 3
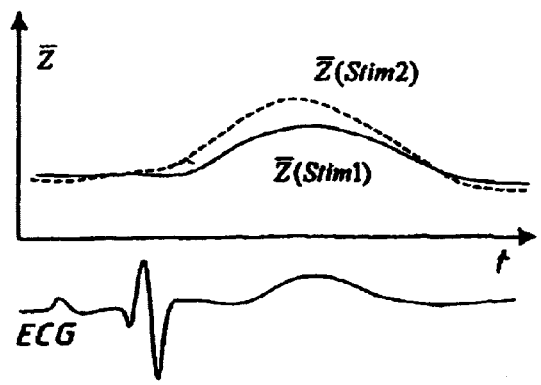
Fig. 4
Fig. 5 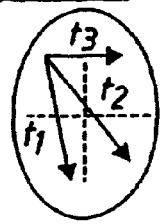 Fig. 6 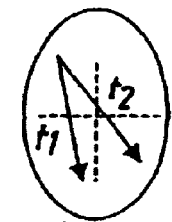 Fig. 7 Fig. 8 Fig. 9 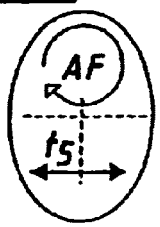

HEART STIMULATOR WITH STIMULATION CONTROLLED BY ANALYSIS OF AN AVERAGE IMPEDANCE MORPHOLOGY CURVE

BACKGROUND OF THE INVENTION

1. Field of the Invention

The present invention relates to a heart stimulator for electric stimulation of a heart, of the type having comprising an impedance measuring unit that measures the impedance between at least two measurement electrodes implanted in a patient such that volume changes of at least one of the chambers of the left heart result in changes in the measured impedance, and an analyzer for analyzing the measured impedance for the control of the stimulation of the heart.

2. Description of the Prior Art

Heart stimulators of this above general type are known. U.S. Pat. Nos. 5,334,422 and 5,584,868 and 6,223,079, disclose cardiac stimulating apparatus for use in heart failure therapy, wherein intracardiac impedance variations are used for sensing the cardiac function. U.S. Pat. No. 4,535,774 discloses a rate responsive pacer which paces at a rate dependent on detected variations in the stroke volume of the heart. One mentioned example of inferring the stroke volume is by use of impedance measurements. For all these known devices the impedance sensing used for controlling the pacing is performed on beat-to-beat bases.

SUMMARY OF THE INVENTION

An object of the present invention is to provide an improved way of controlling the stimulation timing of a heart stimulator to optimize the patient hemodynamics.

The above object is achieved in accordance with the principles of the present invention in a heart stimulator of the type initially described, having a calculation unit which calculates, for a predetermined stimulation pattern, an average impedance morphology curve during a time interval of several cardiac cycles, and an analyzer which analyzes the average impedance morphology curve for use for controlling the stimulation to optimize the patient's hemodynamics.

Thus in accordance with the present invention the measured left cardiac impedance averaged over several cardiac cycles is used for controlling the heart stimulation to optimize hemodynamics.

In an embodiment of the stimulator according to the invention the impedance measuring unit measures real and imaginary (in the mathematical sense) parts of impedance and the calculation unit calculates average values of the real and imaginary parts for use for the control of the stimulation. Blood is resistive and therefore, when the blood volume inside a left heart chamber increases the impedance phase angle will decrease. If, on the contrary, more heart tissue is present the impedance phase angle will become more negative. Therefore, the real and imaginary parts of the measured left cardiac impedance can be used in an advantageous way to optimize hemodynamics of the cardiovascular system. The impedance measuring unit has a measuring circuit preferably in the form of a synchronous demodulator, for obtaining both the real and imaginary parts of the impedance, and the impedance measuring unit can determine the impedance phase angle and the analyzer be adapted analyzes the phase angle for detecting and incipient CHF.

In another embodiment of the stimulator according to the invention the analyzer analyzes at least one predetermined parameter of the average impedance morphology curve for use for the control of the stimulation. A parameter having a value that is primarily dependent on the left ventricular ejection preferably is used. The parameter can be integrated area below the averaged impedance morphology curve versus time, maximum or minimum value of the average impedance morphology curve, the difference between maximum and minimum values of the average impedance morphology curve, the maximum positive or maximum negative slopes of the average impedance morphology curve, or the time between the maximum of the average impedance morphology curve and a predetermined beginning or end of the cardiac cycle.

In a further embodiment of the stimulator according to the invention wherein the stimulator is a multi-site stimulator, the control unit controls the stimulation-timing pattern. Once the optimal stimulation-timing pattern is established the stimulation is continuously adjusted to maintain the same pattern. A stimulation pattern can be considered as a vector of different time intervals and the control unit can first vary the VV-interval while keeping the AV- and AA-intervals constant until first optimum hemodynamics are obtained. The controlling unit then keeps the VV-interval at a constant value equal to the value giving optimum hemodynamics and also keeps the AA-interval constant while varying the AV-interval until second optimum hemodynamics are obtained. The control unit then keeps the AV-interval constant, equal to the AV-value giving the second optimum, and also keeps the VV-value at its above mentioned constant value while varying the AA-interval until third optimum hemodynamics are obtained. The control unit being then keeps the AA-interval constant equal to this AA-value giving the third optimum, and also keeps the AV-interval equal to its above mentioned constant AV-value while again varying the VV-interval until fourth optimum hemodynamics are obtained. The control unit continues this process until the optimums, obtained by the successive variation of these intervals, no longer are improved. It is beneficial to start this process by successively sub-optimizing the VV-interval, the AV-interval and the AA-interval since changes in the VV-interval will affect the hemodynamics more than changes in the AV-interval, and changes in the AV-interval will affect hemodynamics more than changes in the AA-interval.

In this connection it should be noted that the VV timing for patients having Bundle Branch Block is essential for the well being of these patients. It has also been shown that resynchronization in patients having Left Bundle Branch Block improves there quality of life, e.g. improves the maximum oxygen consumption.

In another embodiment of the stimulator according to the invention the electrodes are designed for implantation in the right and left atria respectively or for implantation in the right atrium and left ventricle, the impedance thus measured being a measure of the blood volume of left atrium.

In another embodiment of the stimulator according to the invention the electrodes intended for the left atrium and the left ventricle are designed for implantation in a coronary vein.

DESCRIPTION OF THE DRAWINGS

FIG. 1 is an example of a suitable electrode lead configuration for use in the heart stimulator according to the invention.

FIG. 2 is a block diagram of an embodiment of a heart stimulator according to the present invention.

FIG. 3 illustrates the impedance measured the across the left ventricle during four cardiac cycles with a first stimulation timing, followed by measurements during four cardiac cycles with a second stimulation timing.

FIG. 4 shows averaged left ventricle impedance morphology curves determined for two different stimulation timings, and an ECG.

FIGS. 5, 6, 7, 8 and 9 respectively show different stimulation timing patterns as vectors representing different time intervals.

DESCRIPTION OF THE PREFERRED EMBODIMENTS

Figure 10:
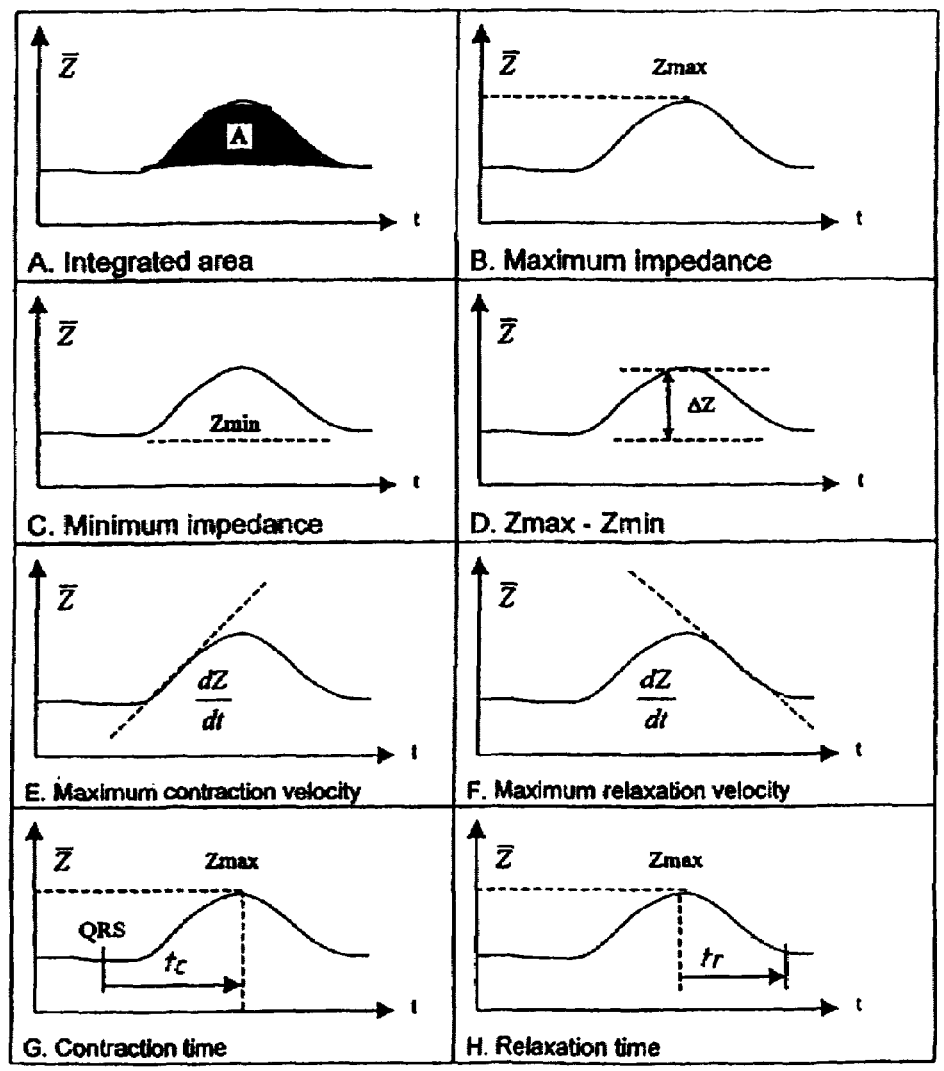
FIG. 10 illustrates different quantities that can be derived in accordance with the invention from the measured left cardiac impedance.

FIG. 1 illustrates suitable electrode configurations making impedance measurements possible at several places of the heart 2. By measuring the impedance between left atrium and right atrium RA electrode leads, or between left ventricle and right atrium leads, or possibly between a left atrium lead and the stimulator case, a signal corresponding to the left atrial blood filling is achieved to be used for hemodynamic optimization of the heart stimulator. A combination of signals obtained from these pairs of electrodes also can be used for this purpose. The left ventricular filling is suitably determined by measuring the impedance between an electrode implanted on the left ventricle and an electrode in the right ventricle. The electrodes intended for left atrium and left ventricle respectively are preferably designed for implantation in a coronary vein in CS. To get a good fixation of the electrode it is beneficial to use a screw-in electrode.

Excessive filling of blood in the left atrium and left ventricle can originate from several different cardiac dysfunctions. According to the invention this can be detected by impedance measurements, and the information obtained from this impedance measurement is used for controlling the stimulation such that hemodynamics are improved by improving the left heart-filling pattern.

FIG. 2 is a block diagram of an embodiment of the heart stimulator according to the invention. A current i(t) is delivered from a current source 21 to electrodes 20, 22 and the evoked voltage response is measured between electrodes 24, 26. The evoked voltage response is amplified in amplifier 28 and with the aid of a reference signal picked up from the current source 21 synchronized in a multiplier 30 with the current. A low pass filter 32 is used to obtain an average voltage signal $u_1(t)$. The corresponding average impedance curve $Z_1$ is given by $$Z_1 = u_1/i$$

The average impedance morphology curve $Z_1$ obtained from a calculation unit 34 is analyzed in an analyzer 36. A control unit 38 is connected to the analyzer 36 to control the heart stimulation pulse generator 40 in response to the output from the analyzer 36 such that patient hemodynamics are optimized.

FIG. 3 illustrates the impedance continuously measured across the left ventricle. The sampling frequency is high enough to make it possible to follow variations during each cardiac cycle, e.g. equal to 128 Hz. During the first four cardiac cycles shown in FIG. 3 stimulation is performed according to a first stimulation-timing pattern Stim1, and during the four subsequent cardiac cycles the stimulation-timing pattern Stim2 is changed.

FIG. 4 shows the average impedance morphology curve Z (Stim1) for a cardiac cycle, calculated during a time interval with a fixed stimulation-timing pattern Stim1. This time interval includes several cardiac cycles, e.g. 10–100 cycles. Thereafter one or more of the timing parameters are changed and a new average impedance morphology curve Z (Stim2) is calculated for a similar time interval. The ECG curve is also shown in FIG. 4.

A quantity that is dependent on the left ventricular ejection is calculated from the average impedance morphology curves, Z cf. FIG. 10 below. By comparing one of these quantities, e.g. the integrated area A, see FIG. 10, for the two timings patterns Stim1 and Stim2 the most favorable of this two timing patterns is selected, and this process can be continued for different stimulation timing patterns Stim such that the area A is maximized as an indication of a maximum stroke volume.

The stimulation timing pattern can be described as a vector of different time intervals $(t_1, t_2, t_3)$, $(t_1, t_2)$ etc., where $t_1$ is the time from right atrial T-wave detection to stimulation in the right ventricle, see FIGS. 5–7. The parameter $t_1$ can also be the time from a right atrial stimulation to right ventricular stimulation that should be selected independently from sensed events. Parameters $t_2$ and $t_3$ denote corresponding right atrium to left ventricle and right atrium to left atrium times respectively. Thus the parameters $t_1$, $t_2$ and $t_3$ define the AA-, AV- and VV-intervals, the parameters $t_1$ and $t_2$ and the quantity $t_2$–$t_3$ defining three different AV-intervals, as appears from FIG. 5.

If it is not possible to stimulate or sense in the left atrium a three-chamber embodiment according to FIG. 6 is selected. If the patient suffers from atrial fibrillation or atrial tachycardia only the two ventricles are involved in the optimization procedure, cf. FIG. 9.

In FIG. 7 the right AV-delay is optimized with reference to left ventricle blood filling. A coronary sinus lead is necessary to measure the left ventricle impedance.

FIG. 8 illustrates a situation where a left ventricular lead is used only for measurement of the impedance Z.

FIG. 10 shows eight examples of quantities, which can be derived from the measured left ventricular impedance. These quantities are integrated area A below the average impedance morphology curve Z versus time t, maximum and minimum values $Z_{max}$ and $Z_{min}$ of the average impedance morphology curve $\overline{Z}$ (diagrams B and C in FIG. 10), the difference $\Delta Z$ between maximum and minimum values of the average impedance morphology curve $\overline{Z}$, (diagram D in FIG. 10), the maximum positive or maximum negative slopes dZ/dt of the average impedance morphology curve $\overline{Z}$ (diagrams E and F in FIG. 10), and the time between the maximum $Z_{max}$ of the average impedance morphology curve-Z and a predetermined beginning (QRS) or end of the cardiac cycle, (diagrams G and H in FIG. 10). The maximum positive slope according to diagram E in FIG. 10 represents maximum contraction velocity of the left ventricle and the maximum negative slope according to diagram F in FIG. 10 represents the maximum relaxation velocity. The time $t_c$ according to diagram G and the time $t_r$ according to diagram H in FIG. 10 represent the contraction and the relaxation times respectively of the left ventricle.

With the technique according to present invention a relatively stable optimum stimulation-timing pattern is obtained which only needs to be checked or verified at, preferably regular, intervals.

Besides the measured cardiac impedance's other quantities and conditions can also be considered for use in optimizing the stimulation-timing pattern. Thus e.g. rate and activity conditions as well as respiratory minute volume can be of importance in connection with optimization of the stimulation-timing pattern.

Although modifications and changes may be suggested by those skilled in the art, it is the intention of the inventors to embody within the patent warranted hereon all changes and modifications as reasonably and properly come within the scope of their contribution to the art.

We claim:

1. A heart stimulator comprising:
   a stimulation pulse generator that emits stimulation pulses adapted to stimulate a heart of a patient;
   an impedance measuring unit having at least two measurement electrodes, and adapted to measure an impedance, having a real part and an imaginary part, between said at least two measurement electrodes resulting from volume changes of at least one left chamber of a heart of the patient, said impedance measuring unit emitting an impedance signal corresponding to said impedance;
   a calculation unit supplied with said impedance signal for calculating, for a predetermined pattern of said stimulation pulses, an average impedance morphology curve from said real part of said impedance signal, and an average morphology curve from said imaginary part of said impedance signal, during a time interval of a plurality of cardiac cycles of the heart; and
   an analyzer supplied with said average impedance morphology curves for analyzing said average impedance morphology curves to generate a control signal for emission of said stimulation pulses to optimize hemodynamics of the patient.

2. A heart stimulator as claimed in claim 1 wherein said impedance measurement unit comprises a synchronous demodulator for generating said real part and said imaginary part of said impedance.

3. A heart stimulator as claimed in claim 1 wherein said impedance measuring unit determines an impedance phase angle from said real part and said imaginary part, and wherein said analyzer analyzes said phase angle to detect insipient congestive heart failure.

4. A heart stimulator as claimed in claim 1 wherein said analyzer analyzes at least one predetermined parameter of said average impedance morphology curve for controlling emission of said stimulation pulses.

5. A heart stimulator as claimed in claim 1 wherein said impedance measuring unit samples said impedance with a frequency allowing impedance variations during a cardiac cycle to be followed.

6. A heart stimulator as claimed in claim 1 wherein said analyzer analyzes at least one predetermined parameter of said average morphology curve selected from the group consisting of integrated area below said average morphology curve versus time, a maximum value of said average morphology curve, a minimum value of said average impedance morphology curve, a difference between a maximum value and a minimum value of said average impedance morphology curve, a maximum positive slope of said average impedance morphology curve, a maximum negative slope of said average impedance morphology curve, a time between a maximum of said average impedance morphology curve and a predetermined beginning of a cardiac cycle, and a time between a maximum of said average impedance morphology curve and a predetermined end of a cardiac cycle.

7. A simulator as claimed in claim 6 comprising a control unit connected to said analyzer for controlling emission of said stimulation pulses to optimize said at least one parameter with regard to hemodynamics of the patient.

8. A simulator as claimed in claim 7 wherein said analyzer analyzes an integrated area below said average impedance morphology curve versus time, as said at least one parameter, and wherein said control unit controls the emission of said stimulation pulses to maximize said integrated area.

9. A heart stimulator as claimed in claim 1 wherein said analyzer analyzes a plurality of predetermined parameters of said average impedance morphology curve, and wherein said heart simulator comprises a control unit connected to said analyzer for controlling emission of the simulation pulses based on a combination of the predetermined parameters analyzed by said analyzer.

10. A heart simulator as claimed in claim 1 wherein said analyzer analyzes at least one predetermined parameter of said average impedance morphology curve, and wherein said heart stimulator comprises an electrode arrangement connected to said simulation pulse generator and adapted to interact with the heart to simulate the heart at multiple sites with a simulation timing pattern, and a control unit connected to said analyzer for controlling said simulation timing pattern to optimize said at least one of said predetermined parameters with regard to the hemodynamics of the patient.

11. A heart stimulator as claimed in claim 10 wherein said stimulation timing pattern includes a VV-internal, an AV-interval and AA-interval, and wherein said control unit executes an optimization procedure comprising varying said vv-interval while keeping said AV-interval and said AA interval constant until first optimum hemodynamics are obtained, and keeping said VV value at a constant value for which said first optimum hemodynamics were obtained while also keeping said AA-interval constant while varying said AV-interval until second optimum hemodynamics are obtained, and keeping said AV-interval at a constant value for which said second hemodynamics were obtained and keeping said VV value at said constant value at which said first optimum hemodynamics were obtained while varying said AA-interval until third optimum hemodynamics are obtained, and keeping said AA-interval at a constant value for which said third optimum hemodynamics were obtained while keeping said AV-interval at said constant value at which said second optimum hemodynamics were obtained while varying said VV-interval until fourth optimum hemodynamics are obtained, and wherein said control unit repeats said optimization procedure until no optimum hemodynamic improvement occurs.

12. A heart stimulator as claimed in claim 11 wherein said control unit controls said stimulation-timing pattern by varying a stimulation rate.

13. A heart stimulator as claimed in claim 1 comprising stimulation electrodes, connected to said stimulation pulse generator and adapted for interaction with the patient to stimulate the heart, said stimulation electrodes forming said measurement electrodes of said impedance measurement unit.

14. A heart stimulator as claimed in claim 13 wherein said stimulation electrodes include an electrode designed for implantation in a right atrium of the heart and an electrode designed for implantation in a left atrium of the heart.

15. A heart stimulator as claimed in claim 13 wherein said stimulation electrodes include an electrode designed for implantation in a right atrium of the heart and an electrode designed for implantation in a left ventricle of the heart.

16. A heart stimulator as claimed in claim 13 comprising a stimulator housing containing said impedance measurement unit, said stimulation pulse generator, said calculation unit and said analyzer, and wherein one of said stimulation electrodes, which also forms one of said measurement electrodes, is designed for implantation in a left atrium of the heart, and wherein another of said measurement electrodes is comprised of a portion of said stimulator housing.

17. A heart stimulator as claimed in claim 13 wherein said stimulation electrodes which form said measurement electrodes include an electrode designed for implantation in a left atrium of the heart and an electrode formed by a portion of said stimulator housing.

18. A heart stimulator as claimed in claim 13 wherein said stimulation electrodes which form said measurement electrodes include an electrode design for implantation in a left atrium of the heart and an electrode design for implantation in a left ventricle of the heart, and an electrode designed for implantation in a coronary vein associated with the heart.

19. A heart stimulator comprising:
- a stimulation pulse generator that emits stimulation pulses adapted to stimulate a heart of a patient;
- an impedance measuring unit having at least two measurement electrodes, and adapted to measure an impedance between said at least two measurement electrodes resulting from volume changes of at least one left chamber of a heart of the patient, said impedance measuring unit emitting an impedance signal corresponding to said impedance;
- a calculation unit supplied with said impedance signal for calculating, for a predetermined pattern of said stimulation pulses, an average impedance morphology curve from said impedance signal during a time interval of a plurality of cardiac cycles of the heart;
- an analyzer supplied with said average impedance morphology curve and determining therefrom an integrated area below said average impedance morphology curve versus time; and
- a control unit connected to said analyzer for controlling emission of said stimulation pulses to maximize said integrated area.

* * * * *